(12) United States Patent
Brown

(10) Patent No.: US 10,548,684 B2
(45) Date of Patent: Feb. 4, 2020

(54) CORNEAL MARKING INK

(71) Applicant: Mindskid Labs, LLC, Wilmington, NC (US)

(72) Inventor: Alan Wesley Brown, Wilmington, NC (US)

(73) Assignee: Mindskid Labs, LLC, Wilmington, NC (US)

( * ) Notice: Subject to any disclaimer, the term of this patent is extended or adjusted under 35 U.S.C. 154(b) by 662 days.

(21) Appl. No.: 15/181,371

(22) Filed: Jun. 13, 2016

(65) Prior Publication Data

US 2016/0361134 A1    Dec. 15, 2016

Related U.S. Application Data

(60) Provisional application No. 62/174,866, filed on Jun. 12, 2015.

(51) Int. Cl.

| | | |
|---|---|---|
| *C09D 11/033* | (2014.01) | |
| *C09D 11/037* | (2014.01) | |
| *C09D 11/322* | (2014.01) | |
| *C09D 11/328* | (2014.01) | |
| *C09D 11/36* | (2014.01) | |
| *A61B 90/00* | (2016.01) | |
| *A61K 49/00* | (2006.01) | |
| *A61F 9/007* | (2006.01) | |
| *A61F 9/013* | (2006.01) | |

(52) U.S. Cl.
CPC ............ *A61B 90/39* (2016.02); *A61K 49/006* (2013.01); *C09D 11/033* (2013.01); *C09D 11/037* (2013.01); *C09D 11/322* (2013.01); *C09D 11/328* (2013.01); *C09D 11/36* (2013.01); *A61B 2090/395* (2016.02); *A61B 2090/3954* (2016.02); *A61F 9/007* (2013.01)

(58) Field of Classification Search
None
See application file for complete search history.

(56) References Cited

U.S. PATENT DOCUMENTS

| 4,875,767 | A  | * | 10/1989 | Wright  | A61B 3/15 351/212 |
|---|---|---|---|---|---|
| 7,431,956 | B2 | * | 10/2008 | Baydo   | A23G 3/0089 426/250 |
| 9,283,117 | B2 | * | 3/2016  | Brown   | A61F 9/0136 |
| 10,201,454 | B2 | * | 2/2019 | Brown   | A61F 9/0136 |
| 2006/0084865 | A1 | * | 4/2006 | Burbank | A61K 49/006 600/431 |
| 2009/0217840 | A1 | * | 9/2009 | Kundakovic | A61K 8/0241 106/31.03 |
| 2010/0121343 | A1 | * | 5/2010 | Stroud | C09D 11/16 606/116 |
| 2010/0298772 | A1 | * | 11/2010 | Moore | A61B 17/3417 604/116 |
| 2012/0013684 | A1 | * | 1/2012 | Robertson | C09D 11/328 347/56 |
| 2012/0176443 | A1 | * | 7/2012 | Robertson | C09D 11/328 347/20 |

OTHER PUBLICATIONS

Lissamine Green B dye; no date available; https://www.sigmaaldrich.com/catalog/product/aldrich/199583?lang=en&region=US; 4 pages.*

* cited by examiner

*Primary Examiner* — Helene Klemanski
(74) *Attorney, Agent, or Firm* — F. Michael Sajovec; Williams Mullen

(57) ABSTRACT

The present disclosure relates generally to dry inks for use in marking the eye prior to surgery and methods of applying the same to eye marking devices. Such inks can include various accepted inks for use on the eye that can be applied to a marking device using relatively fast-evaporating solvents. In this manner, the remaining ink composition can be precisely placed on the eye marking device, and desirably transfer to the marking surface of the eye without dissolving on the journey through the various membranes above the marking surface. Application methods may include use of charged ink particles that may be advantageously manipulated using magnetic fields to even more precisely place the dry ink on a marking device.

14 Claims, No Drawings

CORNEAL MARKING INK

CROSS REFERENCE TO RELATED APPLICATIONS

This present application claims the benefit of U.S. Provisional Patent Application No. 62/174,866 filed on Jun. 12, 2015, the entirety of which is incorporated herein by reference.

FIELD

The application relates generally to improved ink formulations for use on various eye marker tips for marking the eye.

BACKGROUND

This application addresses the problem of longer lasting accurate marks applied to the ocular surface as needed. In the field of refractive surgery there exists a need to place marks on the eye (e.g., ink marks) in order to orient the treatment of astigmatism, among others. In the field of cataract surgery, for example, a corneal astigmatism can be balanced by an intraocular toric lens implant having a curved surface that counterbalances the corneal astigmatism. In such methods for treating astigmatism, the eye should be marked before surgery in order to properly position the treatment of the astigmatism.

Patients undergoing such treatments are ideally required to have the operative site marked with a surgical marker before being brought into the operating room. However, conventional marking devices suffer from issues of, among other things, inadequate ink transfer to the eye surface. Such inadequacy of transfer results principally from the fact that conventional devices are first marked with only a thin layer of wet ink which is then transferred to a wet ocular surface. As a consequence of placing wet ink onto a wet ocular surface, the patient blinks off ink marks from conventional marking devices in a matter of minutes, an undesirably short period of time.

Additionally, it is well known that the eye position rotates or undergoes cyclotorsion when the patient moves from a vertical or sitting position to a lying or horizontal position. The change in position creates an error in marking an eye, and the error can be upwards of 20 degrees, which is clinically significant. As a consequence, the best practice is to mark the patient's eye while the patient is in a vertical or sitting position, because that position is the normal position for use of the eyes. However, this best practice often conflicts with the typical operating room practice of having the patient lying down, prepared for surgery, draped, and ready for the surgeon before the surgeon enters the room. The need to mark the patient in the sitting position delays the normal preparation sequence for surgery.

An alternative practice is to pre-mark a patient in a separate preparation area, in which oral sedation and IVs are generally administered. The pre-marking may be administered with a surgical ink marker pen to the area where the cornea meets the sclera. Such conventional markers leave a lasting dot of ink not found on the thin film of ink applied with conventional sterile metal markers. However the placement of surgical ink marker dots is imprecise and over time the dots tend to smear, creating an undesirable ambiguity of the original intended pinpoint location.

One practice of medicine convention now requires surgeons to mark the patient's brow over the eye having surgery prior to being moved to the operating room. Because every patient gets a correct surgical site identification mark with a surgical marker over the brow, it is convenient for the surgeon to add marks on the eye at the same time. Since conventional metal markers retain only a thin film of ink that is blinked off within minutes, they are not effective for marking outside of the operating room. Consequently, the only lasting marks that can be made before surgery under conventional methods are ink dots placed in the general horizontal and vertical meridians. As noted above, these hand placed dots are not precise and tend to smear over time.

For all the above reasons, the conventional systems for marking the eye for treatment of astigmatism is complex, and suffers from limitations with respect to at least the accuracy of the marks placed, how the procedure is performed, and how the patient is prepared for surgery.

Prior corneal marking devices generally depend on an external source of gentian violet ("GV") ink. In most cases, the GV ink is provided from a sterile GV felt tip pen commonly used to mark the surgical site of patients undergoing various surgeries. The GV ink contained in these pens is generally either a 98% aqueous solution containing 2% GV or a similar aqueous solution of GV with a very small amount of an alcohol solution. Such solutions have long been used with markers for the skin surface but were never intended for use of the relatively sharp edges of a corneal marker.

U.S. Pat. No. 9,283,117, which is fully incorporated herein by reference, describes improved eye marker devices overcoming the shortfalls of the conventional devices and systems for marking the eye for treatment of astigmatism. Such application discloses, among other things, an improved marker device with sharp edges made of various types of material. When the mostly aqueous solution is applied to a metal edge of a corneal marker, the surface tension and surface energy is such that the GV ink tends to bead-up on the marker edge. The conventional mostly aqueous GV on the marker tip is then applied to the cornea. The corneal surface, however, is covered with a tear film composed of 3 separate layers, principally oil, water and mucous. Consequently, a principally aqueous GV layer on the marker tip goes into solution as the tip traverses the 3 layers of the tear film. Only the ink that survives the transit through the tear film can reach the corneal epithelium where vital staining actually occurs. Because this traditional technique uses a wet GV ink to mark a wet cornea, it has been common to see that the marks so placed are generally smeared and easily blinked off, undesirably limiting the duration of visibility of the marks. Limited duration of corneal ink marks places serious constraints on the timing of preoperative corneal marks because the patient must be marked relatively close to the time of eye surgery for the marks to still be visible for use during surgery. These time constraints then interfere with the best patient flow and efficiency for the patients, surgeon, and surgery center. Additionally, if the ink marks are smeared, ill defined, or faint, the final visual result for the patient can be compromised because the surgeon cannot accurately align the treatment of the patient's astigmatism.

For the sake of good patient treatment, and the need for better operating center efficiencies, alternative methods and associated marking inks and devices are needed. Although a primarily wet alcohol-based GV ink formula could overcome some of the issues of wet ink on a wet cornea, it is well known that alcohols are toxic to the corneal epithelium and as such are not favored. Additionally, current 2% GV aqueous based solutions can be applied to a marker tip and left to dry, but the coverage of the marker may be irregular as noted above because of the surface tension and surface energy problems of water on a non-porous edge such as the traditional metal of reusable metal corneal markers. Even non-metallic materials behave similarly with irregular coverage for the same reasons. Further, because of the relatively low concentration of GV molecules in solution that can be located on the marker edge (in view of the limitations discussed above), the ink marks once again suffer from limited longevity. For at least these reasons, improvements in eye marking ink are desired.

In the fields of femtosecond cataract surgery and corneal cross linking, most treatment devices use an infrared camera to visualize the eye. The standard ink used by eye surgeons for marking the eye is GV ink but this ink is invisible under infrared cameras used by a majority of treatment devices. While the ink in a Sharpie™ type marker is visible under the treatment devices' infrared cameras, this ink is not FDA approved. The formula is based on "polychrome" with a quickly evaporating vehicle, both of which have no data concerning safety for use on the ocular surface. Moreover, this unapproved ink has to be placed on the eye with a wet ink marker because the dried ink is adherent to metal or plastic corneal marker tips and will not transfer to the cornea. Accordingly, there exists a need to provide eye surgeons with an infrared visible ink having a known safety profile.

SUMMARY

This application describes improved eye marker ink for use with eye marker devices, such as the devices described in co-pending U.S. patent application Ser. No. 13/427,253, now U.S. Pat. No. 9,283,117. In one embodiment, an approximate 13% GV solution is dried through various means described herein, which will traverse the tear film more intact than an aqueous 2% GV even with some dilution created as a result of the transit through the tear film. In certain other embodiments, a dry ink composition is disclosed that can be used in medical applications, the ink having at least one anhydrous solvent vehicle and at least one pigment that may be selected from the group that includes GV, Rose Bengal, Lisamine Green, Trypan Blue, Brillian Blue, Indocyanine Green, and another biologically acceptable pigment. The pigment can have an amount from about 2% to about 15% by weight of the total ink composition. In some instances, the solvent may be 75% alcohol, or in other instances, 90% alcohol. The composition may further include one or more of iron, pyrolytic carbon, graphene, gold, silver, and/or a chemically conjugated iron/carbon compound, wherein such magnetic carbon compounds are referred herein as "magnetic carbon species."

As used herein, "dry ink" or "dry ink composition" is understood to mean a composition that is initially in substantially liquid form that when subsequently dried (through evaporation in ambient conditions or environmentally controlled conditions (i.e. regulated temperature and/or humidity) leaves a majority of the at least one pigment on the surface from which it evaporated, thereby transferring the pigment in the dry ink from the dry ink composition to a surface to be marked.

Further, the terms "dye" and "pigment" are understood to be used interchangeably and synonymously for purposes of the present disclosure, understanding of course that, for example, GV is a dye and the disclosed iron/carbon pigments are pigments, both of which may be used in various embodiments of the present disclosure to formulate the disclosed dry ink and related method.

The present disclosure further includes a method of applying a dry ink composition to a mammal, the method including exposing an ink solution that includes a pigment in an anhydrous solvent to a temperature sufficient to evaporate at least a portion of the solvent.

Also disclosed is a method of manipulating an ink composition with a magnetic field, the method including application of a dry ink composition that includes one or more of carbon and iron or other magnetically responsive compound, and manipulating the dry ink composition with magnetic force to move the composition. In some embodiments, the magnetic field may be such that it attracts the dry ink composition towards a marking edge of the marking device. In further embodiments, the magnetic field may be such that the dry ink is attracted to the edge of the marking device, but advantages associated with the repulsive nature of the ink itself are utilized to prevent the dry ink from traversing all the way to the marking edge.

DETAILED DESCRIPTION

The present invention will now be described more fully hereinafter, in which embodiments of the invention are shown. This invention may, however, be embodied in many different forms and should not be construed as limited to the embodiments set forth herein. In addition, the sequence of operations (or steps) is not limited to the order presented in the specification and/or claims unless specifically indicated otherwise. Features described with respect to one embodiment can be associated with another embodiment although not specifically described as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that although the terms first and second are used herein to describe various features or elements, these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present invention.

Unless otherwise defined, all terms (including technical and scientific terms) and phrases used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary by +/− twenty percent (20%). The terms "about," "somewhat," etc., with respect to structural or functional inter-relations apart from values or numbers are used to convey that an absolute inter-relation is not required, so as the elements satisfy the described purpose within such inter-relation.

The ink for eye marker tips described herein may be utilized on a variety of eye marker devices, including for example, the eye marker devices disclosed in U.S. patent application Ser. No. 13/427,253, now U.S. Pat. No. 9,283,117.

In one embodiment of the present invention, a more concentrated GV ink solution in a non-aqueous form is disclosed, including in a dry form to enable attachment to a marking tip. Increasing the concentration of the GV and reducing surface tension/energy issues can best be achieved by creating an anhydrous solution of GV.

In various embodiments, a variety of dyes may be utilized for the dry ink compositions disclosed herein including, but not limited to, Rose Bengal, Lisamine Green, Trypan Blue, Brilliant Blue, and Indocyanine Green. In some embodiments, other human-acceptable dyes may be used at various concentrations, including with solutions outside the alcohol-based solutions disclosed herein. GV is more soluble in alcohols than in water. Ethyl alcohol is a primary alcohol for some of the embodiments disclosed herein, but other alcohols such a methyl, propyl, isopropyl, etc. may be used. In some embodiments, GV can achieve an at least 2% concentration in water and/or up to a greater-than approximate 13% concentration when dissolved in 100% anhydrous ethyl alcohol. Other dyes can permit varying concentrations. For example, Indocyanine Green can achieve a greater than approximate 15% concentration when dissolved in anhydrous ethyl alcohol. In one embodiment, one or more pigments are dissolved in an acceptable solvent to achieve between an at least 2% and 15% concentration for later evaporation of the solvent from the tip to leave a greater amount of pigment. In some embodiments, one or more pigments are dissolved in ethyl alcohol at a concentration greater than 15% with advanced means (heat and/or viscosity) to achieve a greater amount of dry ink on the marker tip. In various other embodiments, depending on the solubility of the pigment and/or dye in the solvent, the concentration of solvent could be significantly higher than 15%.

When GV is dissolved in anhydrous ethyl alcohol, surface tension and energy issues of the marking tips are resolved with the solution adhering quickly to various plastics, metals, and other materials in a continuous uniform layer. In various embodiments, a maximum concentration of GV molecules dries quickly to the marker tip due to the relatively fast evaporation of the alcohol.

At higher concentrations of uniform dried GV, the tear film plays a different role relative to the dilutive role seen with weak GV concentrations. With dried GV, the aqueous layer of the tear film rehydrates the dried GV ink, which aids in a focused deposition of the ink in the location where the ink tip is momentarily placed on the corneal epithelium. The direct contact of concentrated ink provides improved staining of the corneal epithelia tissue that can remain visible and in place over, for example, the 2 hours of preoperative drops and/or blinking and preoperative eye sterile prep required before certain surgeries. In some instances, the longevity of the presently disclosed concentrated dried GV corneal marks can provide new efficiencies because, among other things, the patient's eye can be marked well before surgery. The surgeon no longer has to interrupt his or her surgical flow to mark a patient just before the sterile prep. Instead, the patient can be prepped while the surgeon is operating in another room because the corneal marks placed with the dried concentrated GV ink can still be crisp and visible for the one, two, or more hours before surgery. Because the marks remain clear, the surgeon can identify the correct axis of the patient's astigmatism and consequently achieve a better visual result for that patient.

The application to a disposable tip of the presently disclosed concentrated GV ink derived from an anhydrous alcohol solution can take several forms. In some embodiments, the tip edge can be dipped into a bath of the GV solution. However, the great affinity of the anhydrous solution to the plastic may cause a progression of the ink up the tip in a wicking fashion (i.e., capillary action resulting from surface tension of the solution). In various embodiments, the wicking can be reduced by a limited dip in chilled anhydrous GV solution followed by a quick transfer to an increased ambient temperature environment, thereby facilitating relatively quick and complete evaporation of the alcohol component.

In some embodiments, pad printing tools can be capable of transferring an anhydrous solution of ink in controlled amounts to a specific location of a tip edge. Such tools can allow the placement of GV ink in one location and a different colored ink in a separate location. For example, GV and Rose Bengal inks could be applied to the marking tip in alternating bands, thereby allowing the surgeon to use the alternating bands as a measuring device. In one embodiment, two inks with different spectral properties could be placed at different locations. For example, as noted above, some modern femtosecond lasers and corneal cross linking devices use infrared cameras to image the eye. A visible ink, such as, for example, GV, could be placed on the marking tip closer to the center of the cornea where the marks would be used for Toric Intraocular Lens placement, while an infrared visible ink could be placed at the corneal scleral junction to align femtosecond laser surgery without blocking the treatment laser light.

In one embodiment, another mechanism for ink placement may include ink jet printing. An exemplary advantage of inkjet printing over dipping or pad printing is the ability to have more control over the uniformity of the anhydrous solution. In various embodiments, the anhydrous ink solution can be exposed to air with ambient humidity. The hydroscopic properties of the anhydrous ink solution will, over time, absorb water from the air and therefore change the concentration and behavior of the solution. For example, once the GV anhydrous solutions absorbs water to the point that it is only 75% alcohol, the dried GV ink can start to lose its characteristic green metallic sheen and begin to show stress fractures. Fractured dried ink can become dislodged from the plastic marking tip at the moment of marking the eye, creating a chip of dried ink that undesirably breaks off into the tear film. Indeed, a loose chip of dried GV can stain a large area of the cornea and obscure the desired corneal marks. Reducing ambient humidity during the dipping or pad printing process can mitigate some of these risks, but ink jet printing further eliminates the risk of ink concentration drift because the ink reservoir can be protected from ambient humidity. Inkjet printing can also allow an array of different ink solutions to be applied to the marking tip edge in numerous varieties of patterns with greater precision than pad printing.

In some embodiments, the anhydrous GV solution can be chilled either before or after application to a marker tip in order to allow reduced evaporation of the alcohol solvent. In some embodiments, the anhydrous GV solution can be heated either before or after application to the marker tip in order to expedite the alcohol evaporation. Additionally, the temperature and humidity of the environment used for a marker tip drying can be altered to influence the rate of evaporation of the solvent(s), or rate of water absorption into the solvent(s), solution. In some embodiments, an increase of 10 degrees Fahrenheit can accelerate evaporation of the solvent.

In some embodiments, the application process of GV or similar vital dye ink to the edge surface of corneal marking tips may be improved by creating an anhydrous GV solution principally with an alcohol or other anhydrous, but non-toxic, solvent. While the disclosed anhydrous solution of dyes creates crisp corneal marks, the marks can vary in width depending on how much pressure is exerted on the cornea at the time of application of the marker tips. Light pressure generally leaves thin lines while prolonged heavy pressure generally allows more ink to absorb and consequently creates a broader ink mark. Consideration is also given to the anatomy of the corneal epithelium. The epithelial consists of about 5 gelatinous cell layers that are supported by a stiff, underlying Bowman's membrane. In some embodiments, the disclosed ink can adhere to a solid tip that is able to penetrate the corneal epithelium to a 50 micron depth until it encounters the underlying Bowman's membrane. If the ink tip lightly touches the corneal epithelium it may not penetrate all 5 layers and may leave less ink, and a thinner line, than when the tip is pressed firmly to penetrate ink through all 5 cell layers. The treatment of corneal astigmatism requires as much precision as possible because for every 1 degree of error in the placement of a Toric Intraocular Lens, there is a corresponding 3 degree loss of surgical astigmatic effect. Anything that increases the accuracy of the corneal mark will therefore increase the accuracy of the patient's visual result, in some cases by a factor of three or more. Creating an ink tip that allows the application of an ink line as thin as possible provides an accuracy advantage over thicker ink lines.

In some embodiments, the ink disclosed herein can militate against the variable mark width based on variable application pressure, improves the ink application process of corneal marking inks to marking tips, and provides an infrared camera visible marking ink for corneal marking tips.

In some embodiments, a non-toxic ink or pigment is provided that will free surgeons from having to use non-regulatory approved instruments like a Sharpie™ type permanent marker pen. Relatively non-toxic compounds capable of blocking some or all infrared (IR) light incident upon it include various forms of iron and carbon related compounds that can further include micro/nano particle sized carbon, graphite, pyrolytic graphite and the like. Other non-toxic infrared blocking elements could include silver and/or gold. Any or all of these exemplary elements may be used individually or in combination with some or all of the others, and other additional elements or compounds.

Non-toxic forms of iron are found in nature and are a key ingredient in cell physiology with the iron containing hemoglobin molecule of a red blood cell being one example. Carbon and carbon based molecules are the building blocks of life. In general, carbon is harmless, and as such, has found significant use in the cosmetic industry in mascara, eyeliner, eye shadow, and other such products. Graphite represents sheets of carbon molecules held together by weak covalent bonds. Pyrolytic graphite has a similar structure but with slightly different bonding that gives it conductive and magnetic properties. Graphite derivatives such as graphene could also be used for IR blocking but is currently price prohibitive. Although any of these or similar elements/compounds could be used as an infrared blocking pigment/ink, there exists an advantage to use a combination of both iron and carbon, in some embodiments, because the carbon can provide a desirable combination of a visible and infrared visible ink, while the association of iron allows unique opportunities to use magnetism in the application of the ink to the tip and the transfer of the ink to the eye.

An inexpensive and functional ink formulation according to some embodiments of the present disclosure includes iron and carbon and/or carbon derivatives, and allows for the advantages of broad spectrum visibility in addition to the ability to manipulate the location of the ink through the use of a magnetic field. As with GV, an iron/carbon formulation can use some form of alcohol as a vehicle for applying the ink to corneal marking tips. The use of an alcohol can favorably affect the surface tension/energies with an iron/carbon formulation, as it does with GV.

Whether the application method is dipping, pad print transfer, or inkjet spray, there exists a short time period of time where the ink formulation is on the corneal marking tip in a liquid form. In some embodiments, it is during this brief time when the iron/carbon formulation is still in a liquid state that an applied magnetic field can be used to direct the iron of the formulation towards the sharp edge of the corneal marking tip. In various embodiments, a corneal marking tip can have two sides which meet at the marking edge. When a magnetic field is applied to the liquid formulation, the iron/carbon complex, the formulation can be drawn towards the magnetic field. For example, if the negative pole of a magnet were held in relative proximity to the marking tip edge, the iron of the iron/carbon complex would be drawn with a positive polar charge towards the negative pole of the magnet, and so be drawn towards the edge of the corneal marking tip. However, as the positively polarized iron/carbon complex approaches the edge boundary on both sides of the marking tip, the repulsive positive to positive interaction of the two sides can take meaningful effect. More particularly, the iron/carbon complex can align towards the marker edge, but will not cover the actual edge because of the repulsive forces associated with the positive charges. As the particles get close to the edge they start to repel each other and so create a "boundary line" where the particles will less readily approach the marker edge due to the repulsion of like positive charges as they approach each other.

The boundary edge of the iron/carbon formulation may become locked in place as soon as the alcohol (e.g., chromatography grade) or other solvent carrier vehicle evaporates. The iron/carbon boundary edge becomes an ink edge that is no longer subject to the possibility of becoming too wide as might occur with GV alone because the infrared visible portion of the iron/carbon ink is essentially absent at the tip edge due to the above noted similar pole magnetized iron repulsion. When the marker tip is pushed onto the corneal epithelium, the actual marker edge may have no significant iron/carbon ink, but because both sides of the edge have a boundary line of the iron/carbon complex, the boundary line comes into contact with the epithelium and penetrates the tissue a depth determined by the iron/carbon complex. The result is two thin iron/carbon black lines with an intervening gap of no ink. In some embodiments, GV can be applied to the marker tip prior to or simultaneously with the iron/carbon complex. Doing so will provide a very visible purple blue edge line that has the two boundary limited thin black lines of the iron/carbon complex on either side of the central GV line.

The strength of the magnetic field can impact the boundary line location which can be used to direct that boundary line location in 3 dimensions. This can prove useful for corneal marking used in femtosecond laser procedures where an ink that is visible under an infrared camera is needed but it is also desirable for the infrared component of the ink to be limited to the lateral edge of the corneal marker. Since an infrared blocking ink has the potential to block some of the energy of an infrared range laser, the infrared ink used for alignment is typically best placed on the lateral corneal scleral junction so as to not interfere with the effect of the laser. The magnetic properties of an iron/carbon formulation allow the manipulation of an infrared boundary line to the lateral edge of the marker tip. In some embodiments the iron or other magnetically responsive compound can be chemically conjugated to the carbon to insure that the advantageous properties of both are simultaneously directed by an applied magnetic field.

Manipulating the magnetic field strength or direction can be useful in positioning an ink formulation that uses iron or any other magnetically responsive material. In some embodiments, a single broad magnetic field is applied to both sides of the marker tip at once to create an ink boundary line a fixed distance from the edge of the marker tip. In some embodiments, the iron complex is directed to the very edge of the marker tip by applying the iron complex to just one side of the of the marker tip, allow it to dry and then apply the opposite side using an opposite polarity magnetic field. In such cases the edge of one side could be positively charged towards the tip edge and dried in place. The opposite side could be inked with a negative polarity towards the tip and so be attracted to the dried positively charged particles.

Ink placement may also be manipulated by the varying the composition of the magnetic ink complex. In various embodiments, different magnetic carrier compositions may include iron and other non-toxic magnetic compounds. In one embodiment, pyrolytic graphite combines both the properties of magnetic attraction and the infrared blocking of carbon in one compound. Additionally, while various embodiments of the present invention disclose a free ink complex in an alcohol vehicle, similar results could be obtained from microencapsulated magnetic ink complexes in a variety of alternate vehicles. Chromatography grade alcohols may be used to further limit the amount of residual trace compounds after complete alcohol evaporation.

What is claimed is:

1. A dry ink composition suitable for applying onto an eye, the composition comprising:
    at least one anhydrous solvent vehicle adapted to dry through evaporation in ambient conditions or environmentally controlled conditions; and
    at least one pigment or dye selected from the group consisting of GV, Rose Bengal, Green S, Trypan Blue, Brilliant Blue, Indocyanine Green, the at least one pigment present in an amount of from about 2% to about 15% by weight of the total ink composition;
    wherein the dry ink composition is initially in a substantially liquid form that when subsequently dried leaves a majority of the at least one pigment on a surface from which it evaporated, thereby allowing subsequent transferring of the pigment or dye to an eye surface to be marked and whereby a tear layer of the eye surface rehydrates the dry ink composition.

2. The dry ink of claim 1, wherein the solvent comprises at least 75% alcohol.

3. The dry ink of claim 1, wherein the solvent comprises at least 90% alcohol.

4. The dry ink composition of claim 1 further including a non-toxic infrared blocking pigment adapted to block at least some of incident infrared light.

5. The dry ink of claim 4, wherein the non-toxic infrared blocking pigment comprises iron.

6. The dry ink of claim 4, wherein the non-toxic infrared blocking pigment comprises carbon.

7. The dry ink of claim 4, wherein the non-toxic infrared blocking pigment comprises pyrolytic graphite.

8. The dry ink of claim 4, wherein the non-toxic infrared blocking pigment comprises graphene.

9. The dry ink of claim 4, wherein the non-toxic infrared blocking pigment comprises a chemically conjugated iron/carbon compound.

10. The dry ink of claim 4, wherein the non-toxic infrared blocking pigment comprises gold.

11. The dry ink of claim 4, wherein the non-toxic infrared blocking pigment comprises silver.

12. A method of marking a mammalian eye comprising the step of applying the dry ink composition of claim 1 to a mammalian eye with a marking device.

13. A dry ink composition suitable for applying onto an eye, the composition consisting essentially of:
    a solvent; and
    a pigment selected from the group consisting of GV, Rose Bengal, Green S, Trypan Blue, Brilliant Blue, Indocyanine Green or a combination thereof, whereby the pigment is present in an amount of from about 2% to about 15% by weight of the total ink composition,
    wherein the dry ink composition is initially in a substantially liquid form that when subsequently dried leaves a majority of the at least one pigment on a surface from which it evaporated, thereby allowing subsequent transferring of the pigment to an eye surface to be marked and whereby a tear layer of the eye surface rehydrates the dry ink composition.

14. A method of marking a mammalian eye comprising the step of applying the dry ink composition of claim 13 to a mammalian eye with a marking device.

\* \* \* \* \*